(12) United States Patent
Keene et al.

(10) Patent No.: US 11,266,189 B2
(45) Date of Patent: Mar. 8, 2022

(54) ANTI-MICROBIAL, DISINFECTION CHAMBER RESPIRATORY FACE MASK/SHIELD

(71) Applicants: Sharon A. Keene, Tucson, AZ (US); Benjamin J. Davenport, Chaparral, NM (US)

(72) Inventors: Sharon A. Keene, Tucson, AZ (US); Benjamin J. Davenport, Chaparral, NM (US)

(*) Notice: Subject to any disclaimer, the term of this patent is extended or adjusted under 35 U.S.C. 154(b) by 0 days.

(21) Appl. No.: 17/169,253

(22) Filed: Feb. 5, 2021

(65) Prior Publication Data

US 2021/0298391 A1    Sep. 30, 2021

Related U.S. Application Data

(60) Provisional application No. 62/994,523, filed on Mar. 25, 2020, provisional application No. 63/143,677, filed on Jan. 29, 2021.

(51) Int. Cl.
*A41D 13/11* (2006.01)
*A61L 2/10* (2006.01)

(52) U.S. Cl.
CPC ...... *A41D 13/1192* (2013.01); *A41D 13/1107* (2013.01); *A61L 2/10* (2013.01); *A61L 2202/11* (2013.01); *A61L 2202/20* (2013.01)

(58) Field of Classification Search
CPC ... A41D 13/1192; A41D 13/1107; A61L 2/10; A61L 2202/11; A61L 2202/20
See application file for complete search history.

(56) References Cited

U.S. PATENT DOCUMENTS

| 5,165,395 A | 11/1992 | Ricci |
| 8,733,356 B1 * | 5/2014 | Roth ........................ A61L 9/20 |
| | | 128/205.27 |

(Continued)

FOREIGN PATENT DOCUMENTS

| DE | 20 2021 100 057 | 3/2021 | |
| GB | 2548012 A * | 9/2017 | ........... A61N 5/0616 |
| TW | M244921 | 1/2004 | |

OTHER PUBLICATIONS

International Search Report and Written Opinion issued in PCT International Patent Application Serial No. PCT/US21/17124, dated May 3, 2021 (10 pages).

(Continued)

*Primary Examiner* — Regina M Yoo
(74) *Attorney, Agent, or Firm* — Hayes Soloway P.C.

(57) ABSTRACT

A self-sterilizing, face mask, respirator, open or enclosed face shield employs germicidal, far UV-C light safe for direct human exposure, mitigating risk of acquisition or transmission of respiratory pathogens, such as COVID 19. Device attachments or special lenses direct far UV-C light into the respiratory chamber and/or reservoir areas of infection including nasal, oropharyngeal or ocular areas to reduce or eliminate pathogens, serving also as a treatment modality. In a preferred embodiment the face shield has a removable front section, which can be exchanged or replaced with sections that include various functional attributes while maintaining germicidal protections and avoiding need to remove PPE during these activities including consumption of liquids, oral medications or food, as well as providing antimicrobial absorbent sneeze or cough guard or rhinorrhea secretion absorption, or a communication device to address communication deficiencies caused by respiratory protection barriers.

6 Claims, 9 Drawing Sheets

(56) References Cited

U.S. PATENT DOCUMENTS

| | | | |
|---|---|---|---|
| 10,335,618 B2* | 7/2019 | Zhou | A62B 18/02 |
| 10,709,944 B2* | 7/2020 | Bonutti | A63B 60/46 |
| 11,000,624 B1* | 5/2021 | Babcock | A61L 9/20 |
| 2009/0014002 A1 | 1/2009 | Krafthefer et al. | |
| 2010/0132715 A1 | 6/2010 | Litz | |
| 2016/0001108 A1 | 1/2016 | Zhou et al. | |
| 2016/0074683 A1 | 3/2016 | Bergeron et al. | |
| 2018/0169279 A1* | 6/2018 | Randers-Pehrson | A61L 2/10 |
| 2018/0264161 A1 | 9/2018 | Welch | |
| 2020/0215214 A1* | 7/2020 | Rosen | A61L 2/24 |
| 2021/0162089 A1* | 6/2021 | Zimmermann | A62B 23/025 |

OTHER PUBLICATIONS

Welch, David et al., "Far-UVC light: A new tool to control the spread of airborne-mediated microbial diseases" *Scientific Reports*, Feb. 9, 2018, 7 pages.

Coolhill, Thomas et al., "Overview of the Inactivation by 254 nm Ultraviolet Radiation of Bacteria with Particular Relevance to Biodefense" *Photochemistry and Photobiology*, Apr. 17, 2008, 84: 1084-1091, 7 pages.

Stathis, Christopher et al., "Review of the use of nasal and oral antiseptics during a global pandemic" *Future Microbiology*, (2021) 16(2), 119-130, 12 pages.

"NIH study validates decontamination methods for re-use of N95 respirators: Three methods effectively sanitized masks for limited re-use" Media Advisory, Apr. 15, 2020, 2 pages.

"Upper-Room Ultraviolet Germicidal Irradiation (UVGI) COVID-19" cdc.goc/coronavirus May 20, 2021, 4 pages.

* cited by examiner

ANTI-MICROBIAL, DISINFECTION CHAMBER RESPIRATORY FACE MASK/SHIELD

CROSS REFERENCE TO RELATED APPLICATION

This application claims priority to U.S. Provisional Patent Application Ser. No. 62/994,523, filed Mar. 25, 2020 and U.S. Provisional Patent Application Ser. No. 63/143,677, filed Jan. 29, 2021, the contents of which are incorporated herein by reference.

BACKGROUND OF THE INVENTION

1. Field of Invention

The present invention relates to antimicrobial face masks/face shields to prevent spread of infectious diseases. The invention has particular utility in connection with personal protective equipment (PPE's) such as face masks and face shields and will be described in connection with such utility.

2. Description of Related Art

Surgical masks, respirators and face shields help mitigate the spread of infectious diseases including, but not limited to the common cold, influenza, SARS, H1N1 Swine Flu, and most recently, COVID-19, aka "coronavirus" or SARS-COV2. Respirators and masks, including surgical masks, and face shields are designed to reduce the spreading of airborne illnesses by providing a physical filter between facial regions which connect to the respiratory tract of the user and the user's ambient environment. Respirators add additional protection via air filtration of pathogens. Surgical masks are less effective than respirators, as they are primarily a barrier to splash and splatter, with modest to minimal protection to pathogenic aerosols. Respirators can provide a tighter seal around the nose and mouth and better air filtration. Because surgical masks are also less effective than respirators at reducing the spread of viral or other microbial infections via aerosolized particles, they can be a risky form of personal protective equipment for health care providers dealing with influenza, COVID-19, and for other microbial pandemics. Effective prevention of the spread of airborne illnesses is particularly important for healthcare providers and first responders, who frequently come into contact with infected and non-infected patients. However, protecting members of the general public from respiratory pathogens is also important to reduce infectious disease morbidity and mortality, as well as hospital and health care duress during a pandemic. Face shields provide a physical barrier to splatter, but by being open to ambient air around the edges, cannot protect against aerosolized virus or small floating droplets. Face shields must be enclosed to offer any real protection against respiratory pathogens in the air.

Despite the effectiveness of recently developed COVID vaccines, the flurry of newly identified mutations make it prudent to have other options to help protect the population from respiratory pandemic and reduce the spread of disease, while helping to ease the burden on the healthcare system. Common masks that are used by non-medical professionals are paper or cloth masks, which are only partially effective at reducing the spread of viral or other pathogen infection through inhalation and exhalation. Paper masks are not regulated and while they have been established as more effective than no barrier, their efficacy is variable, with only 30-50% barrier efficacy in some instances, which may provide users a false sense of security leading them to acquire or spread infection. These unregulated masks typically are not multi-ply and do not provide significant respiratory protection from aerosolized pathogens. Paper masks are mainly useful at preventing the user from touching the area around their nose and mouth and create some barrier to droplets. Such common paper and cloth masks are marginally useful for preventing a patient from contracting infection or from preventing an infected patient from spreading infection. Nevertheless, for aerosolized virus, research suggests unregulated masks offer better protection against viral pathogens than no mask at all. During times of pandemic when personal protective gear may be rationed due to high demand, the need for a continuous supply of replacement masks, respirators and face shields places financial and medical strains on the health care system.

Surgical masks are loose-fitting and disposable, and often wrap around the ears to cover just the nose and mouth. Most surgical masks are multi-ply, providing better filtration than cloth or homemade masks. Some surgical masks have an additional face shield. Surgical masks are regulated, unlike cloth or paper masks, and reduce the risk of contracting or spreading infection by filtering out a degree of small particles such as viruses. Surgical masks are used by doctors, surgeons, and dentists during medical procedures for maintaining a sterile procedure in non infectious environments and preventing fluid transmission between healthcare providers and patients. However, in times of respiratory pandemic there is still risk of infection transfer as these surgical masks have been shown to have reduced efficacy reportedly around 80% of particles for air filtration, which aids in reducing but not completely stopping the spread of viral pathogens either via exhalation or inhalation. On a routine basis, surgical masks also serve as a barrier to liquid splashes including saliva. However, surgical masks do not cover eyes to prevent ocular transmission of aerosolized pathogens. Surgical masks are frequently worn in East Asian culture, including in Japan and Taiwan, to reduce the risk of spreading infection and as a sign of social responsibility to alert others that the person may be infectious.

Respirators provide further protection against bilateral spread of infection—preventing the wearer from being exposed to infection and preventing an infected person from transmitting infection to others. The most common respirators are the disposable N95-N100 respirator masks. Respirators under optimal circumstances are designed to be tight-fitting around the nose and mouth area when adherent to skin, and filter out small particles including virus so that inspired air is largely purified from microbes. Respirators, when perfectly fitting, may filter out 95%-100% of airborne particles as small as 0.3 microns. Respirators, in conjunction with other personal protective equipment are highly effective at reducing the spread of viral and bacterial pathogens and are commonly used by research and medical professionals. However, there are inherent limitations of the effectiveness of the masks including respirators, for example, when used by wearers who have facial hair, who experience perspiration on the face that limits the occlusive fit of the mask, or who's facial shape does not allow a perfect or secure fit or who feel claustrophobic and frequently touch or adjust the mask to breathe better, potentially contaminating it or reducing efficacy by admitting non purified air into the respiratory chamber of the mask. Furthermore, even with optimal fit, none of these options provides adequate protection against the force of a sneeze or cough if the wearer is infected, where forceful aerosols can permeate all current types of masks and respirator barriers. In the case of COVID 19 the virus is extremely small at less than 0.2 microns making an adjunctive means of anti-microbial protection within the respiratory chamber of a mask or face shield, a desirable goal. Furthermore, currently there are no effective PPE options to allow wearers to remain protected while they consume food or liquid, to communicate unconstrained, to address their own infection symptoms without removing their own PPE or that may actually treat them if they become exposed. Improving the antimicrobial milieu of the breathing chamber inside a face shield will be improved first of all by making it enclosed, and secondly, providing adjunctive effective anti-microbial technology. A need remains to overcome the limitations of the imperfect mask or respirator and to improve the antimicrobial environment of an enclosed face shield type respiratory barrier while offering a new mode of antimicrobial treatment.

Importantly, some respirators, including the N95 mask, are disposable, in order to eliminate the opportunity for daily contamination when exposed to infected persons or patients, and to avoid the potential spread of infection between health care providers or spreading infection between patients via cross contamination. It is assumed respirators become contaminated when doctors come into contact with infected patients, particularly for aerosolized types of infection—or when worn by an infected person. Unfortunately, in the event of a shortage of personal protective equipment, including face masks, respirators and face shields, healthcare providers and first responders are forced to reuse disposable PPE, increasing the likelihood of becoming infected themselves and of spreading infection to others. Conventional respirators when worn properly by a person infected with viral, bacterial, or fungal pathogens decrease the spread of their droplets by keeping them trapped in the face cup. However, these devices do nothing to decrease the level of infectious pathogens already present on skin or in viral reservoirs of an infected person's nasal or oral cavities. In fact, face masks on an infected person in some instances may actually create the moist environment that could increase viral replication.

Face shields provide ocular protection that face masks do not. They also allow a more social visage of the wearers face during communication which can be more soothing to patients in times of pandemic and allow more social interaction between members of the public if they opt to wear protective gear in public, they can also offer the ability to positively identify a person in situations when this is important (hospitals, clinics, banks or other commerce etc). However, conventional face shields are not enclosed and do not filter air or protect the wearer from aerosolized pathogens such as COVID 19 aka SARS-COV2.

Powered Air Purifying Respirators (PAPR) are generally more effective than N95 respirators, utilizing battery operated blowers to blow air through filtration cartridges for effective purification against a wide variety of pathogens and particulates and have assigned protection factors (APF) of at least 25. These devices offer an enclosed respirator, and may come with loose fitting headgear such as hoods and helmets and can be worn with a limited amount of facial hair. Most of the PAPR components can be cleaned, disinfected, and re-used and shared and may offer less breathing resistance compared to N95 masks. However, limitations of use in the healthcare setting include cost, limited downward vertical field of view, blower noise and head covering which impairs a wearers ability to hear, reduced ability to use a stethoscope, need for replacement batteries, and need for proper disinfection and cleaning after each use or contamination exposure. Such systems despite efficacy would not be considered readily useable for general public use due to noise, bulkiness and need for specialized disinfection procedures after contamination exposure. Furthermore, the appearance of such head gear in these and other types of protective respirators can be anxiety provoking to patients or other members of the public. Furthermore, all current masks, respirators and shields constrain communication to some degree by the inherent unintended acoustic barrier provided by these forms of PPE which cover the mouth and nose. All current masks, respirators and shields must be removed during consumption of food, drink or medication leaving users exposed during these activities. Currently healthcare workers during pandemic emergencies work many hours without food or drink in order to avoid removal of scarce, disposable PPE. Furthermore, none of the masks, respirators or shields assist persons experiencing rhinorrhea or cough to deal with these issues without removal of the PPE, which exposes the user to contaminating the air and people around them A need for a more effective, comfortable, socially useful, visually non-threatening and personally identifying method of portable respiratory protection from aerosolized pathogens exists.

Ultraviolet (UV) light is known to cause damage and destruction to DNA of microbial pathogens and is effective to sterilize surfaces making it useful as a topical germicidal method in health care settings such as hospitals and clinics, as well as laboratories, pharmaceutical clean rooms, and water purification systems, to name a few examples. UV light is divided into three main wavelength ranges, UV-A (315 nm-400 nm), UV-B (280 nm-315 nm), and UV-C (100 nm-280 nm), all of which have certain germicidal properties; however, certain wavelengths also are known to have human cell toxicity. For example, UV light at certain wavelengths causes damage to eyes and skin including sunburns, and the DNA damage accrues to human cells as well which ultimately can lead to skin and other cancers. Recently, however, a wavelength subset of UV-C light, known as far UV-C light (207-222 nm) has been shown to kill bacteria, viral and fungal pathogens, but is not absorbed by even the outer layers of the skin or the tears in the human eye obviating the risk of damage to eyes and skin providing the opportunity to utilize the antimicrobial properties of UV-C light without the dangerous side effects.

Researchers studying the far UV-C phenomenon postulated its benefits as an environmental germicidal agent which could be useful in cleaning pathogens from the air in buildings, for example, by its use in public buildings as an overhead antimicrobial light. An additional suggestion by scientists would be its public use in airplanes, where the plane could become sterilized, either periodically throughout the flight, or during the time between flights. However, far UV-C light has not been utilized as part of personal protective equipment as a direct sanitizer for skin or other tissue areas, such as the nose and throat as a means to directly prevent and even treat infection, where exposure to the light serves the dual purpose of anti-microbial protection for an uninfected user, as well as a therapeutic modality to reduce viral burden and act as an infection containment device for an infected user. Furthermore, when far UV-C light is used in close proximity to the target (face/nose/mouth), ozone free, light sources such as LEDs manufactured or appropriately attenuated to emit far UV-C light waves can be used without the toxicity associated with other UV-C wavelengths outside this range that are absorbed. Illuminating the region between the inner mask and surface of the skin with far UV-C light is a safe resonant frequency for human tissue. This arises from an inherent characteristic of all objects known as "resonant frequency," which is the frequency at which an object naturally vibrates. Applicant's mask device targets the virus and other pathogens, and the far UV-C shakes apart—the structures by entering the pathogen, injecting energy that will damage the pathogen's cellular function so that it will not be able to grow. Accordingly, the present inventions are a two-factor protection system, the material of the mask creates a filtration barrier and the resonant frequency of far UV-C light destroys any ambient pathogens that escape through the barrier effectively sterilizing the respiratory chamber. Of note, in the far UV-C light region, human tissue remains unaffected given the $H_2O$ frequency is outside far UV-C light band of focus for the mask or shield system. By the judicious use of far UV-C wavelengths of electromagnetic energy, unwanted pathogens are destroyed, mask material faults are overridden, and far UV-C light purified air intake is controlled in such a way as to safely and effectively halt the acquisition or transmission of pathogenic microorganisms. Additionally for the wearer who has become infected, the topical application of far UV-C light to infected reservoirs could be anticipated to reduce or eliminate viral burden and either prevent, eradicate or reduce severity of illness.

Earlier applications of UV light in protective masks such as described in U.S. Pat. No. 8,733,356 to Roth for an antimicrobial protective mask with UV-C light emitting diodes in the wavelength range of 240-270 nm for sanitizing air being breathed by the wearer to detoxify respired air, is specifically designed to avoid direct light exposure to the wearer. This configuration specifically referred to the creation of a separate "recess" or passageway in its design which creates a shield to avoid UV-C light exposure to the wearer, describing the UV diodes to "pivot away" from the nose and mouth. The apparent intention was to circulate air through the protective recess or passageway, for the purpose of antimicrobial air sterilization in such a way as to avoid exposure of the wearer to the toxicity of the UV-C light in the 240-270 nm wavelength on their skin. Specifically, UV-C light in the 240-270 nm wavelength would be expected to be injurious to skin, eyes and other human tissues. Roth's mask design reflected this understanding. Specifically, the air would pass through or in front of a lighted recess or 'duct' system that circled the nose and mouth—but would not directly expose the wearer's skin (or presumably eyes) to the UV-C light. Furthermore, Roth did not design his mask to utilize UV light to target potential viral reservoirs, such as nasal passages or the oropharynx, or peri ocular areas for the purpose of reducing viral and bacterial pathogens in these structures—the latter as a therapeutic maneuver, not only a protective one.

Accordingly, a need exists for a self-sterilizing germicidal face mask, respirator or enclosed face shield to create a respiratory chamber that not only protects the wearer from external pathogens, but optionally may be used to reduce pathogens on the skin and inside the nose and oropharynx or around the ocular areas of the wearer as both protective and a treatment modality. The nasal cavity and mouth contain structures that are often reservoirs or entry areas for viral or other pathogenic microbes. There has been a need for a method of decreasing viral load in reservoir areas to reduce acquisition or transmission of pathogens while also potentially reducing severity of disease. Moreover, there has been an unmet need for a type of face mask, respirator or enclosed face shield that can self-sterilize to reduce the volume of disposable personal protective equipment needed by health care professionals or members of the public during a pandemic as well as to potentially increase access of regular antimicrobial respirator masks to members of the public who would gain greater protection against exposure to air borne and aerosolized infectious pathogens, compared to cloth masks, particularly during times of pandemic.

Furthermore, many wearers of face masks complain of a sense of claustrophobia from the limited air space of respirator type masks, resulting in constant manipulation and touching which reduces its utility as a barrier, and increases contamination risk. For these people an enclosed face mask or shield with a larger respiratory chamber may offer more comfortable use, making it more likely to provide protection from acquisition or transmission of disease.

Members of the public and particularly patients can feel anxiety by the appearance of many respirator type masks and head gear. PAPR machines are large and bulky, and sometimes the blowers are noisy. A need exists for less threatening appearing, effective pathogen protection. Furthermore, the ability to see a person's face and positively identify them is advantageous and necessary for proper medical care of individuals, in banking situations or various other forms of commerce where this may be necessary, or social settings where a person's visage is comforting and socially advantageous but the need for protection against respiratory acquisition or transmission remains.

SUMMARY OF THE INVENTION

The present invention in one aspect provides a face mask, respirator, open or enclosed face shield comprising one, several or arrays of light sources such as Light Emitting Diodes (LED's), manufactured or attenuated to emit wavelengths in the far UV-C range (currently defined as 207-222 nm), and to avoid ozone production on the inside/facial side of the mask, in order to create a germicidal breathing chamber inside the nose and mouth cup of the mask or shield and reduce or effectively eliminate the inhalation of pathogens by the wearer that can occur if ambient air escapes into the mask, including viral particles and bacteria, and also effectively reduces the transmission of pathogens from an infected wearer. The mask may be fitted near the nasal area with LED's manufactured or attenuated, to be non ozone producing far UV-C emitting light from LED's or other light sources, or with moveable or attachable "wands" or an internal built in or attachable far UV-C emitting lighted ring that can be directed toward the nasal passages and oropharynx for the purpose of reducing or eliminating viral or other pathogen burden on the user's skin, oropharyngeal or nasal passages and may include a detachable far UV-C emitting wand or stylus which can be directed toward pathogen reservoir or ocular areas Alternatively, lenses on the light source can direct the far UV-C light beams toward the nasal and oral cavity as well. The self-sterilizing germicidal properties of far UV-C light allows the user to re-use their mask, respirator or face shield without risk of acquisition or transmission of infection even if worn in the presence of people who are infected. The addition of the far UV-C light can turn any current disposable mask, respirator or face shield into re-useable PPE alleviating the current shortage. Furthermore, the malleable nose ring containing far UV-C light can be built in or made as an "add on" malleable nose attachment to be used in or with any mask, respirator, shield or directly attachable to the nares.

The present invention in another aspect provides an enclosed face shield comprising one or several or an array of light sources such as LED's manufactured or attenuated to emit non ozone producing, far UV-C light (range 207-222 nm) on the inside facial side of the mask, in order to create an anti-microbial respiratory chamber inside the face shield to reduce or effectively eliminate the inhalation and acquisition of pathogens by the wearer, including viral particles and bacteria, while also effectively reducing the transmission of pathogens during exhalation from the wearer. The enclosed face shield may be configured with a continuous occlusive fit closely along the forehead, temples, lateral cheeks, jawline and at or beneath the chin of the wearer, and may include a sectioned lower chamber with a removable/replaceable mid-section of the shield around the nose and mouth, with replaceable sections each of which may provide a variety of accessory functions such as a cough-sneeze guard; a rhinorrhea rolling absorbent anti-microbial pad; a resiliently deformable aperture or one way valve to allow admission of a straw or tube for liquid consumption; or a larger deformable self-sealing or mechanically sealing aperture for oral medications or eating; or a Radio-Frequency (RF) wireless communication microphone/auditory amplifier configured in such a way to provide privacy between close communicants, and to allow answering land line phone calls, with variable volume control for addressing even large audiences or classrooms in order to achieve improved communication while maintaining anti-microbial protection. The RF technology can be configured to allow cellular network communications, obviating the need to remove protective gear while answering cell phones or participating in large group communication.

All far UV-C embodiments in this invention provide an unexpected result over the prior art in that the related art tries to avoid direct damaging UV-C exposure to the skin or eyes, since broad spectrum UV-C light has known DNA toxicity, and is known to be carcinogenic when targeted to skin and damaging to eyes. However, far UV-C light (currently defined as 207-222 nm) is not harmful to human skin, as it does not penetrate the outer most layer of skin or even tears in the human eye. This invention therefore improves over the prior related art in that it not only purifies inhaled air, it is engineered in a way to reduce viral or other target pathogen burden in exhaled air in an infected user and can be used to reduce pathogens in the user's likely pathogen reservoirs, the nose and throat or oropharynx, and ocular areas via exposure to far UV-C light (currently defined as 207-222 nm) at various effective dosing. The invention further engenders the novel result that emitting far UV-C light, rather than broad spectrum UV-C light, has unique beneficial effects of safely reducing pathogens on the skin or other tissues, due to the properties of the specific range of wavelengths when utilized in this unique design and configuration for personal protective wear. The known properties of light support the advantage of close proximity of the far UV-C light source such as LED's to target areas, allowing more accurate and consistent dosing compared to previously suggested ambient treatment modalities. For example, being close to the target allows for a low power far UV-C light source such as an LED which in turn, can be made to avoid ozone production which can result from photolysis of oxygen from far UV-C wavelengths at higher power.

The present invention provides a respiratory face mask or enclosed respiratory chamber face shield that can also self-sterilize internal and external surfaces for reusability and enhanced ability to avoid cross contamination, reduce pathogens on the skin and inside the nose and mouth or around ocular areas by targeting far UV-C light (inside the mask or shield), also creating a disinfecting chamber for inhaled or exhaled air. In an exemplary embodiment of the invention, the respirator, face mask or enclosed face shield comprises a facial surface and an exterior surface, one or more or an array of light sources manufactured or attenuated to emit far UV-C wavelengths disposed on the facial surface of the face mask or enclosed face shield, and a battery powered switch disposed on the external surface of the face mask or face shield, wherein activation of the switch activates the one or more or an array of light sources manufactured or appropriately attenuated to avoid ozone and emit light in the far UV-C range in continuous or pulsatile modes. In other embodiments, the face mask may further comprise a malleable ring with two lighted wands, in which far UV-C emitting light sources on the wand or ring may be directed as desired to the nasal passages or oropharynx of the wearer. Specific lenses can also be used to direct stationary light sources if the far UV-C emitting light source is built into the mask, respirator, or face shield. Additionally, by providing far UV-C light from a source such as diodes directed on the external or internal surface of the mask or shield, such lighting can sterilize both external and internal surfaces of the mask or shield for repeat use. In other embodiments, an enclosed face shield includes far UV-C, non ozone producing light from any appropriately attenuated light source such as LEDs, to sterilize the air and larger breathing chamber of the enclosed respirator shield. The face mask, respirator, or face shield may be made self-disinfecting through the use of a plurality of far UV-C lights on the external and internal surfaces of the mask or shield. However, in a preferred embodiment the shield or mask may be made of clear constituents allowing light on the interior or exterior to irradiate both sides of the mask and sterilize their surfaces. The enclosed face shield may contain moveable or detachable wands or stylus to direct light into reservoir areas of the nose and oropharynx, as well as toward ocular regions, alternatively lenses can be used to direct light to target areas. Exposure of the wearer to far UV-C light may be continuous or pulsed with power and dosing adjusted to achieve optimal germicidal efficacy for a specific pathogen.

The invention further relates to a method of administering far UV-C light to the skin, nasal passages, and inside the oropharynx or around the ocular area to reduce the risk of contracting infection if pathogens are introduced, as well as reduce the burden of pathogens in an already infected person thereby possibly reducing both the severity of disease and spread of infection.

Another advantage of this invention is the ability to self-sterilize a face mask, respirator or face shield/enclosed face shield for reusability in order to prevent shortages of personal protective equipment for healthcare providers and first responders, or improve access to infection protection to members of the general public and to obviate the need to change or handle contaminated gear. The enclosed face shield may be entirely constructed of clear materials to allow light to permeate both sides of the device for decontamination. The presence of external light sources manufactured or attenuated to emit far UV-C light or a stylus containing them allows the user to target the external light to any target in their path (e.g., a countertop, door knob, hands). The enclosed face shield offers multiple advantages over current masks and respirators, with an overall larger more secure respiratory chamber with 2 factor respiratory decontamination, and also with a removable/replaceable lower section with varied accessories for permitting the wearer to have a sneeze or rhinorrhea guard, to consume liquids, a method to allow users to target far UV-C light on food or drink before it is ingested, and to consume food or oral medication—without removal of the personal protective apparatus, also a modality for improved communication in the presence of a respiratory barrier that can also create a communication barrier. In a hospital setting the face shield may also have an air tight opening for passage of an endotracheal tube or suction apparatus, to allow access to the respiratory tract while minimizing exposure to hospital personnel. The face shield without enclosure attributes can also be used with a conventional N95 mask or other filtration masks with the added safety of far UV-C light for germicidal air purification; or as an enclosed, respiratory chamber face shield with an anti-microbial filtration system, which would provide any wearer, in effect, an ambulatory isolation room for their head.

Still another advantage of the present invention is that it provides a therapeutic option via the ability to direct far UV-C light topically into the nose and oropharynx or around the ocular areas, to eradicate viral and other pathogens directly in their reservoirs or where they find entry into the human body, while a wearer may be infected, asymptomatic or pre-symptomatic and ambulatory and moving about socially. Decreasing the viral load in anatomic reservoirs has been correlated with reduced transmission of disease and disease severity, while increasing the rate of recovery of infected patients.

The mechanism of the removeable section in the front of the enclosed face shield, may include mechanical attachments, or the use of rare earth magnets, which can also act as a viral attractant during inter changing of the sections. Attracted virus or other pathogens can then be deactivated by the far UV-C lights. Further attributes of the attachments or face shield materials may include embedded particles such as copper, for added anti-microbial protection.

BRIEF DESCRIPTION OF THE DRAWINGS

The foregoing, and other features and advantages of the invention, will be apparent from the following, more particular description of the preferred embodiments of the invention and the accompanying drawings, wherein like numerals depict like parts, and wherein.

DETAILED DESCRIPTION OF THE EMBODIMENTS

Figure 1:
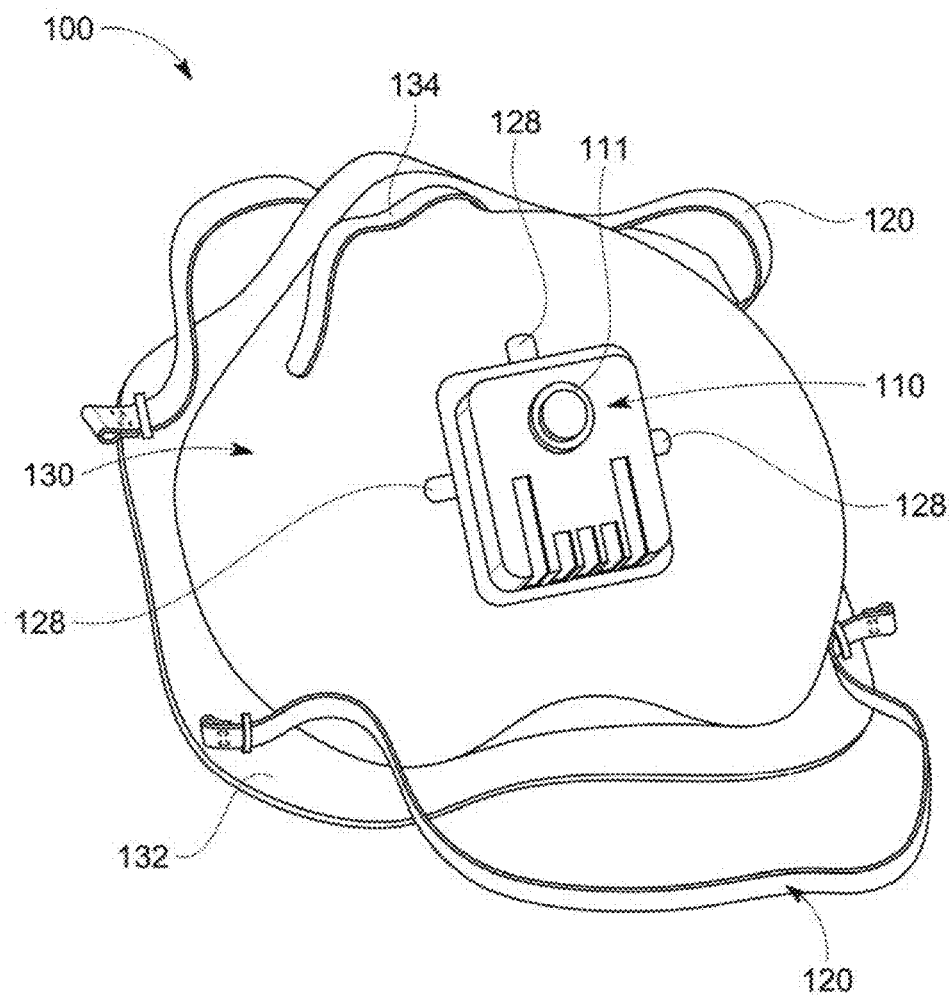
FIG. 1-2 are outer and inner views of face mask according to one embodiment of the invention.

Preferred embodiments of the present invention and their advantages may be understood by referring to the drawing figures. Further features and advantages of the invention, as well as the structure and operation of various embodiments of the invention, are described in detail below. Although the invention is described in the context of a face mask, respirator or face shield, the inventive techniques described herein can be implemented as any face mask, respirator, face shield, or enclosed face shield including surgical masks or cloth masks. The efficacy of the application of far UV-C light in an open face shield would not provide the two factor protection of a filtered and enclosed face shield.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

As used herein "far UV-C light" means UV light waves identified to not penetrate the skin or eyes of a person exposed to it and non toxic for human exposure in certain doses having a wavelength currently identified in the range of 207-222 nm.

Moreover, the described features, structures, or characteristics of the invention may be combined in any suitable manner in one or more embodiments. It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents. Reference will now be made in detail to the preferred embodiments of the invention.

The present invention provides a face mask, respirator or face shield/enclosed face shield creating a respiratory chamber fitted with various embodiments of light sources manufactured or attenuated to emit far UV-C wavelengths that can self-sterilize and reduce or safely eliminate microbes including viruses, algae, fungi, molds, yeasts, or other pathogens in the air, on the skin and inside the nose and mouth of the wearer by targeting far UV-C light directly to the respiratory chamber, skin, nasal passages, oropharynx and ocular area. In one aspect a respiratory face mask or face shield comprises an interior surface and an exterior surface; one or more light sources manufactured or attenuated to emit far UV-C light into the interior of the face mask or face shield; optionally one or more light sources configured to direct far UV-C light onto the exterior surface of the face mask or face shield and a switch preferably disposed on the external surface of the face mask or face shield. Activation of the switch activates the one or more far UV-C light sources. The invention further relates to a method of administering far UV-C light to the air and surface of the respiratory chamber, skin, nasal passages, and inside the mouth or toward the ocular area to reduce the level of pathogens in order to reduce acquisition or transmission of infection, and optionally onto the interior and exterior surfaces of a face mask or open or enclosed face shield to sterilize these surfaces for continued use.

Light waves are affected by ambient altitude, therefore, an altitude sensor may be used to make filter adjustments to insure that the range of wavelengths in the mask, and respirator or shield remain in the far UV-C range.

Combining far UV-C light technology with an open or enclosed face shield or any face mask or respirator allows a greater degree of anti-microbial protection than any of the masks, respirators or face shields currently available and helps to overcome some of the limitations of this PPE by providing an additional mechanism for germicidal protection. Furthermore, intermittent targeted far UV-C inside masks, respirators or face shields may aid in reducing viral burden in reservoirs when they occur. In the case of a clear face shield type respiratory chamber, maintaining a more social appearance for the user with improved breathing comfort may encourage their use in social settings outside the hospital or clinic. A clear face shield or respirator or mask allows far UV-C light to penetrate both sides to self sterilize against a particular pathogen making the device reusable. A more social appearance encourages the public to take measures that reduce their risk for contracting illness, or transmission of symptomatic or asymptomatic disease. Face shield accessories including improved communication, food, liquid or medication consumption, or ability to cough or address a runny nose while maintaining personal and ambient protection from respiratory contamination, provide previously unavailable functionality in PPE that are advantageous to healthcare personnel as well as the public at large.

Figure 2:
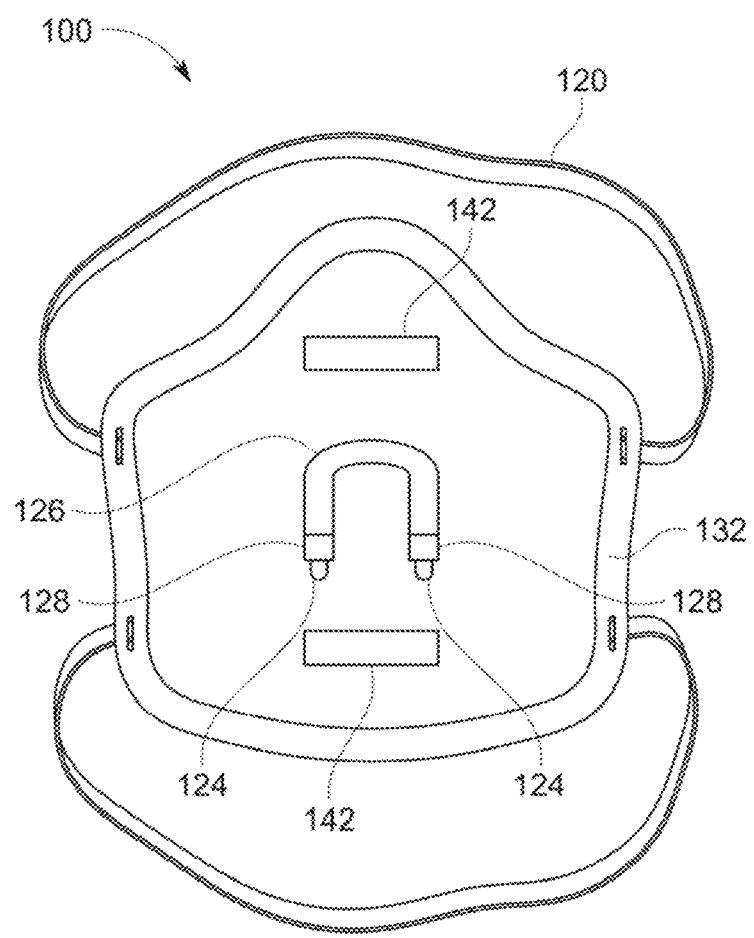
Figure 3:
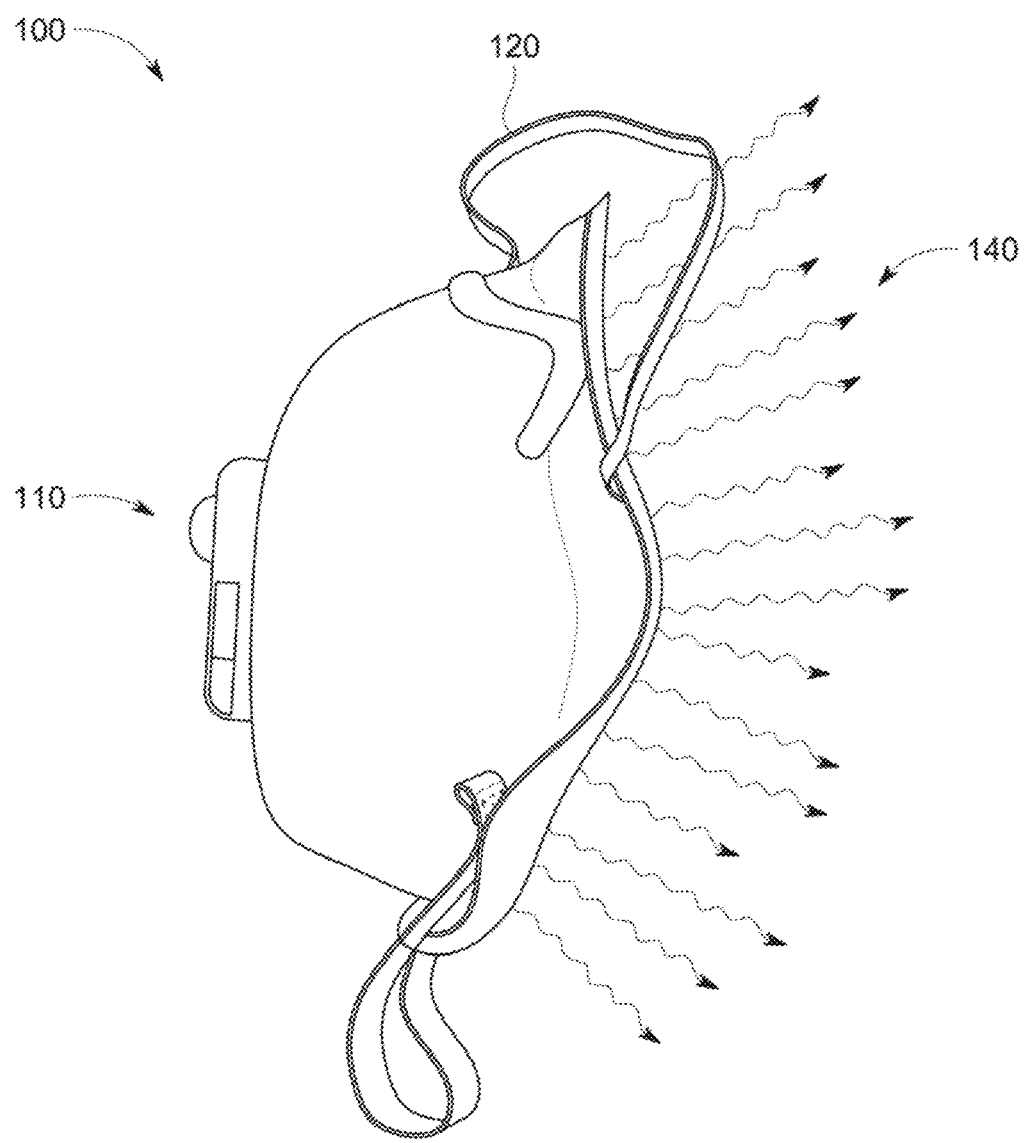
FIG. 3 is a side view of a face mask of FIGS. 1 and 2, and showing any light source manufactured or attenuated to emit non ozone producing, far UV-C light waves on the facial side of the mask according to an embodiment of the invention.

FIGS. 1-3 illustrate a respiratory face mask 100 with a push button on the external side of the mask according to an embodiment of the invention. The respirator 100 comprises power source including a battery and circuit within a module 110 including light sources manufactured or attenuated to emit far UV-C light, and having an on-off switch (sealed push button switch) 111 on the external surface of the mask and flexible bands 120 that wrap around the back of the head to secure the face mask to the user. Module 110 may have a single or variable power modulator to allow a range of low dosing, for example but not limited to, 0.8-2.0 $mJ/cm^2$ from the far UV-C light source such as LEDs which can destroy influenza, or at ~3 $mJ/cm^2/hr$ which has been determined to inactivate SARS-COv2 within minutes. Other virus, or target pathogens will require specific dosing adjustments. In a preferred embodiment, the far UV-C light waves in the mask may be transmitted through an LED or other light source within a u-shaped ring or similar malleable attachment 126 with two or more detachable far UV-C diode or similar wands or stylus 128, allowing the directional use of the far UV-C light to direct beams directly into nasal or oropharyngeal passages where the viral or other pathogenic particle reservoirs reside. The u-shaped or other shaped far UV-C emitting ring can be built in, or attached by a clip to a pre-existing mask or respirator or directly to the nares. The face mask, respirator or face shield also includes one or a plurality of light sources manufactured or attenuated to emit far UV-C light 124 onto the facial and internal/external surfaces of the face mask or respirator, alternatively lenses may be used to direct the light into nasal or oro-pharyngeal passages. During use, the wearer also may periodically open their mouth while far UV-C light is being transmitted to reduce viral load and kill pathogens if present, or as prophylaxis against asymptomatic infection. The mask may further be self-sterilizing, by providing one or a plurality of light sources emitting far UV-C light 128 configured to direct far UV-C light onto an exterior 130 of the face mask in order to sterilize all surfaces of the mask. The mask may further comprise a skirt 132 around the edges and a nose clip 134 to form fit to the user's face.

FIG. 3 is a side a view of the face mask 100 of FIGS. 1 and 2 and shows an example of the far UV-C light beams 140 paths.

Multispectral sensors can be used in the face shield to adjust wavelengths according to skin pigment and altitude variations to insure they are the desired far UV-C wavelength.

Figure 4:
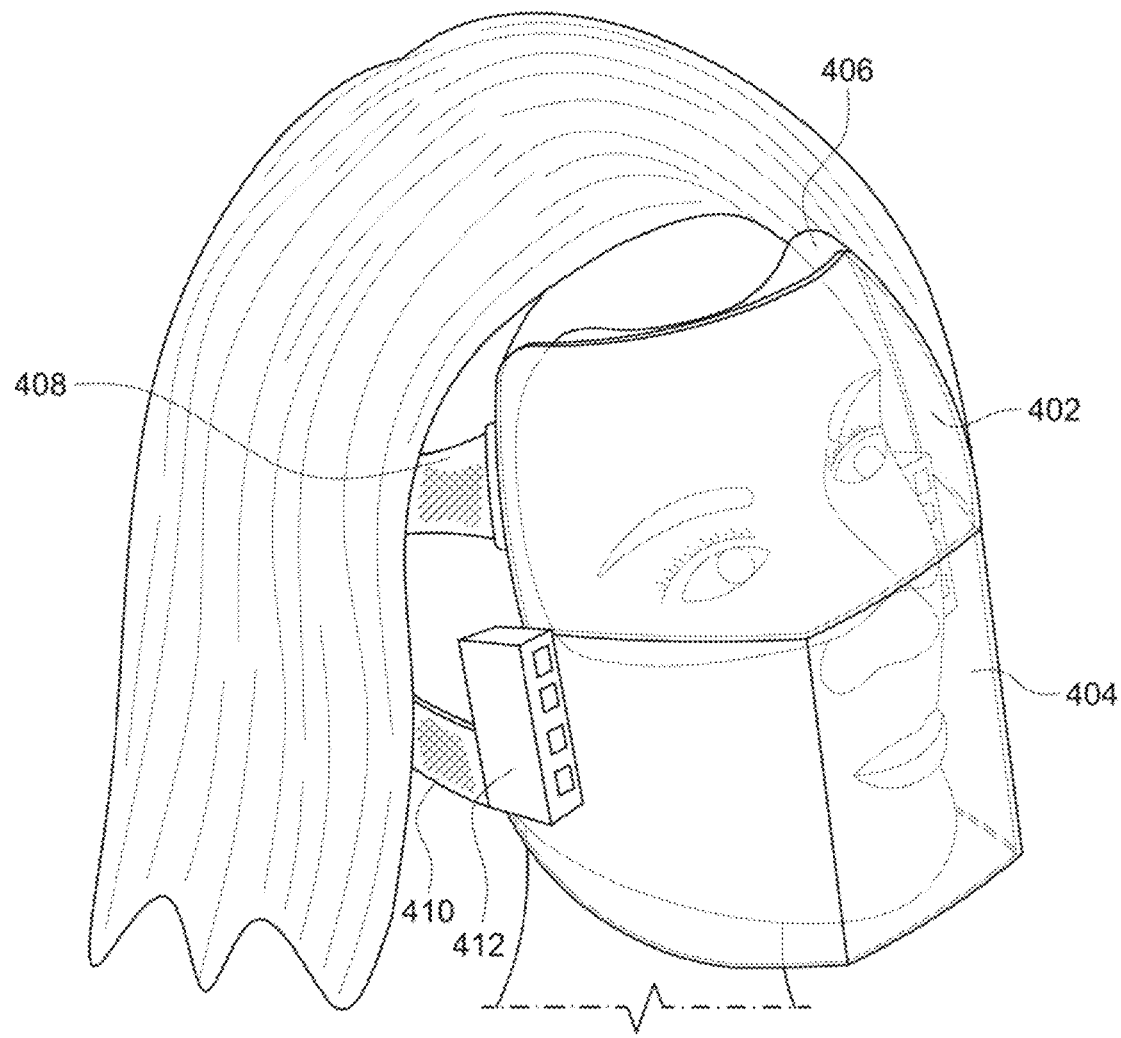
FIGS. 4 and 5 are perspective views of an enclosed face shield in accordance with one embodiment of the present invention.
Figure 5:
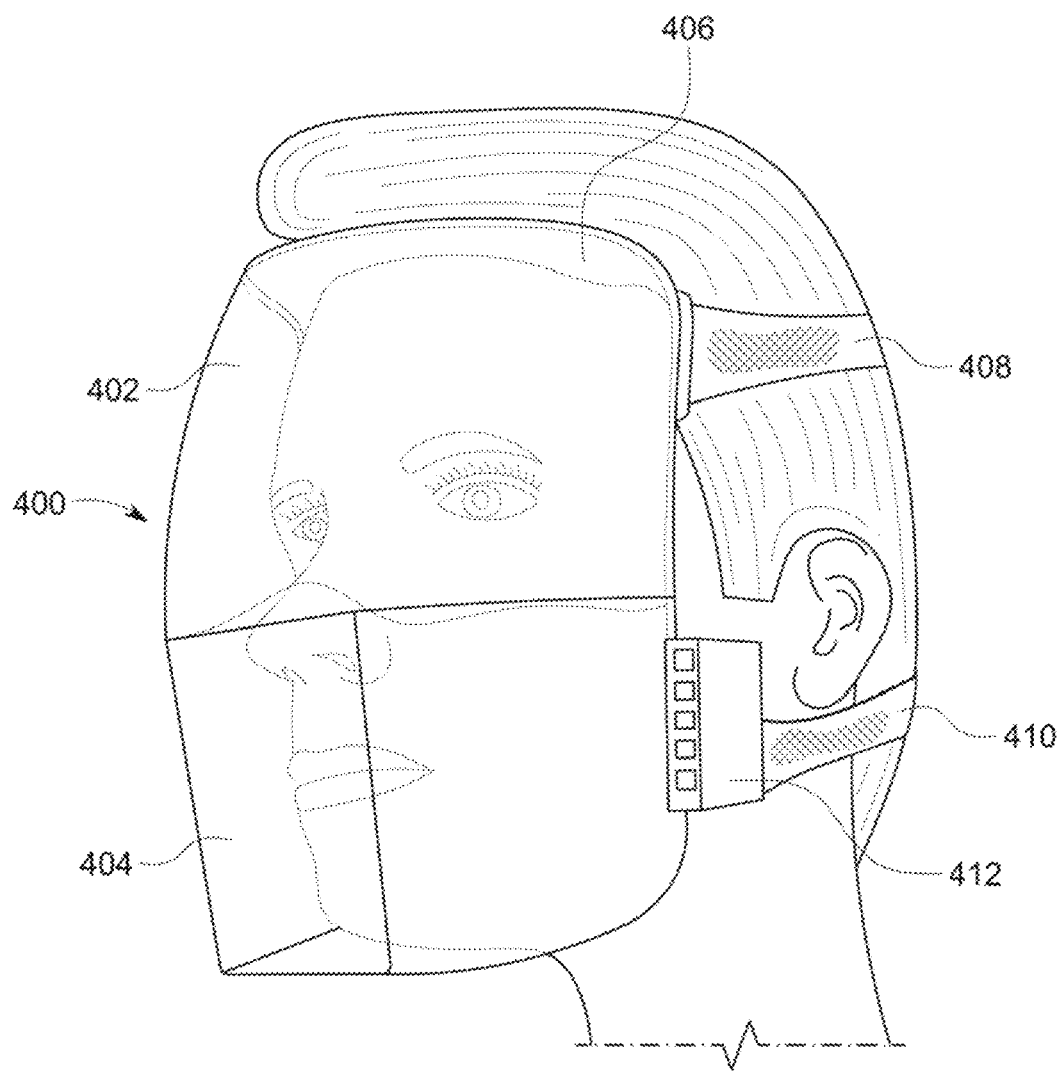

Referring to FIGS. 4 and 5, there is illustrated a face shield 400 in accordance with another embodiment the present invention. Face shield 400 comprises curved brow section 402 configured to substantially conform with a wearer's forehead, and a lower face section 404 configured to cover the nose and mouth of the wearer. In order to increase comfort to the wearer, the brow section 402 and the lower face section 404 are padded with a soft deformable occlusive padding 406 allowing a shelf to hold the face shield a specified distance away from the face and skin in order to create a respiratory chamber, and to allow adequate space for ventilatory apertures, and air filtration. A pair of adjustable head straps, or other apparatus 408, 410 are provided for holding the face shield 400 to the head of the wearer. Alternatively, the face shield 400 may be configured to be attached to a helmet, cap or hat or other head covering or secured by clear head bands or head harness or bands like the stems of reading or safety glasses.

Face shield 400 is formed of a transparent plastic or other transparent material, and includes a battery powered module 412 similar to module 110 discussed above, powering one or more far UV-C light sources directed into the interior, and optionally onto the exterior of the face shield. In a preferred embodiment light sources 420 (see FIG. 6) are mounted adjacent the top of the head shield, and directed downwardly to flood the interior of the face shield with far UV-C light. Various lenses may also be used to direct or focus light toward desired targets. Furthermore, air inlet fenestrations surrounding the face shield may be further enhanced with HEPA or other anti microbial type filtration attachments or with activated charcoal filters. A one-way exhaust valve 424 on the shield will be situated below the mouth, in front of the chin, to aid in removal of exhaled CO2.

Figure 6:
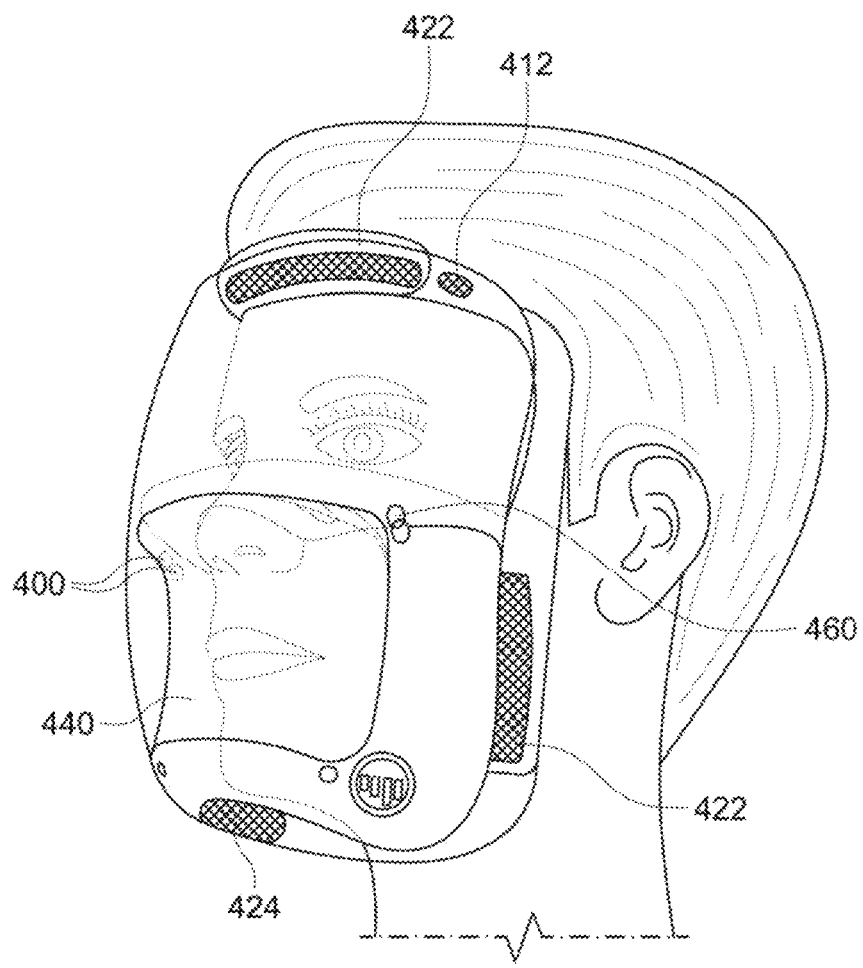
FIGS. 6 and 7 are perspective views of a face shield in accordance with another embodiment of our invention.
Figure 7:
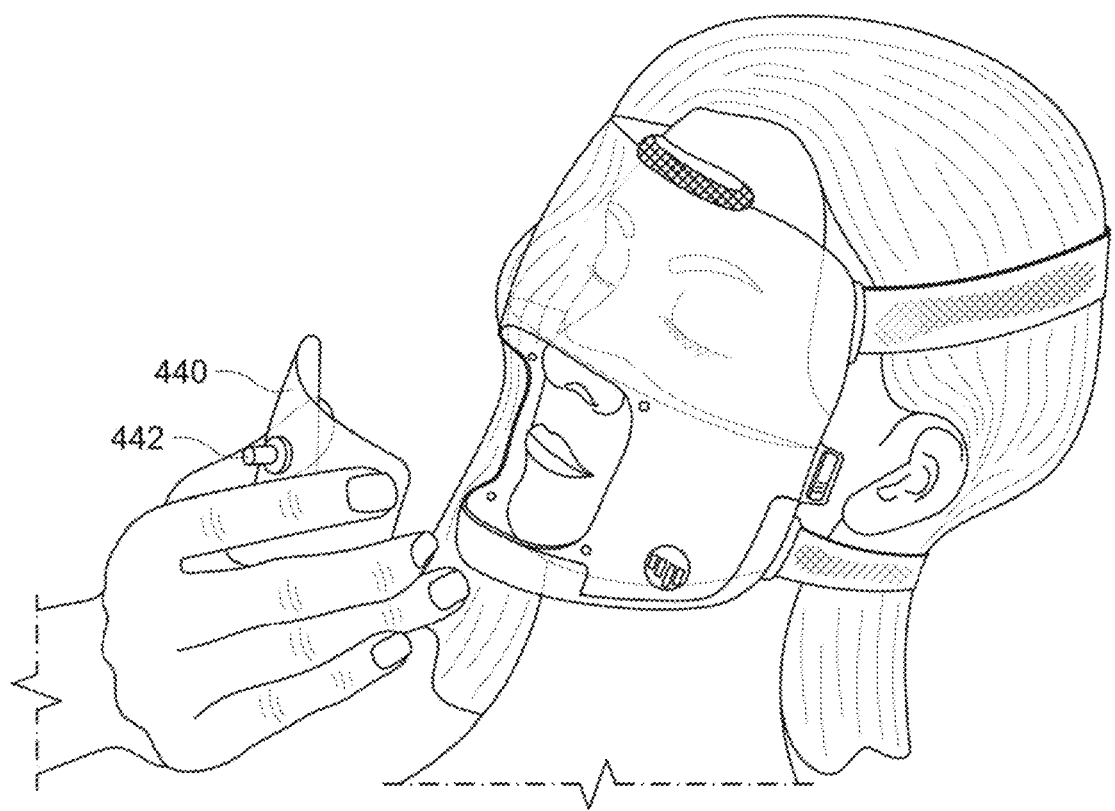
Figure 8:
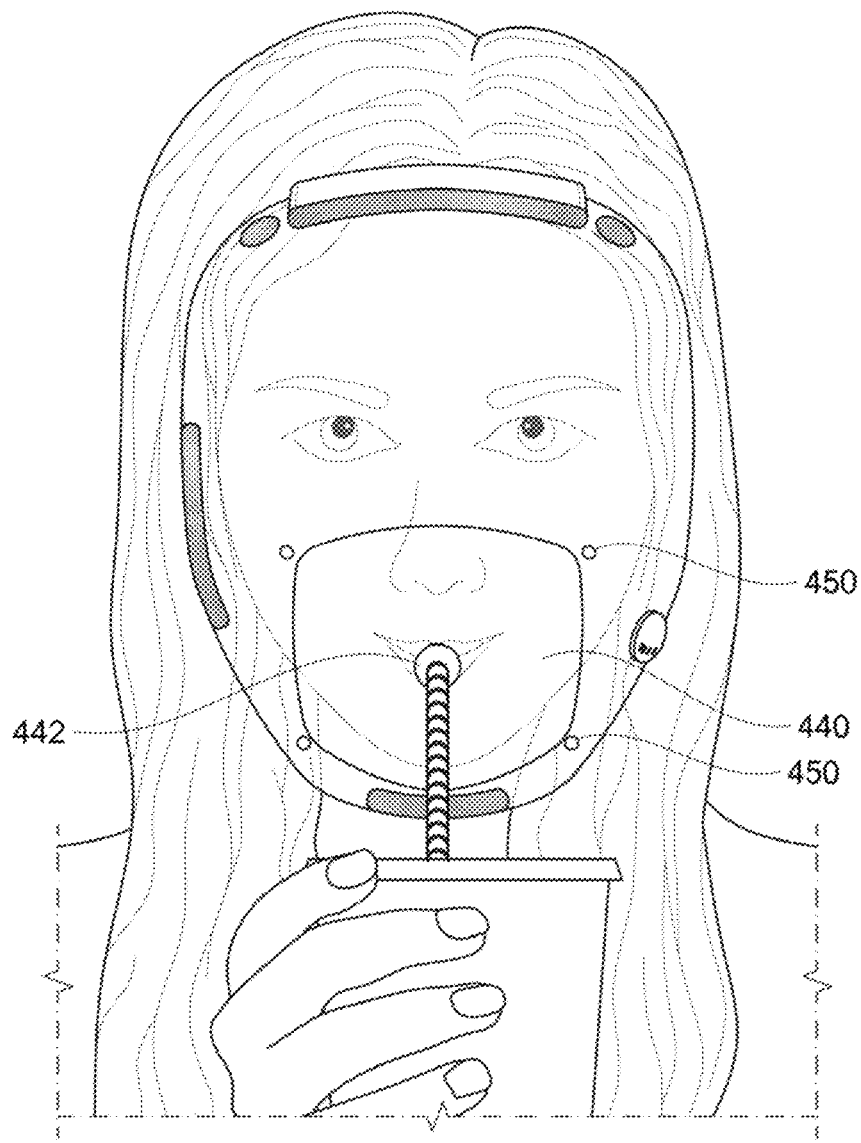
FIGS. 8 and 9 are perspective views of still other embodiments of our invention.
Figure 9:
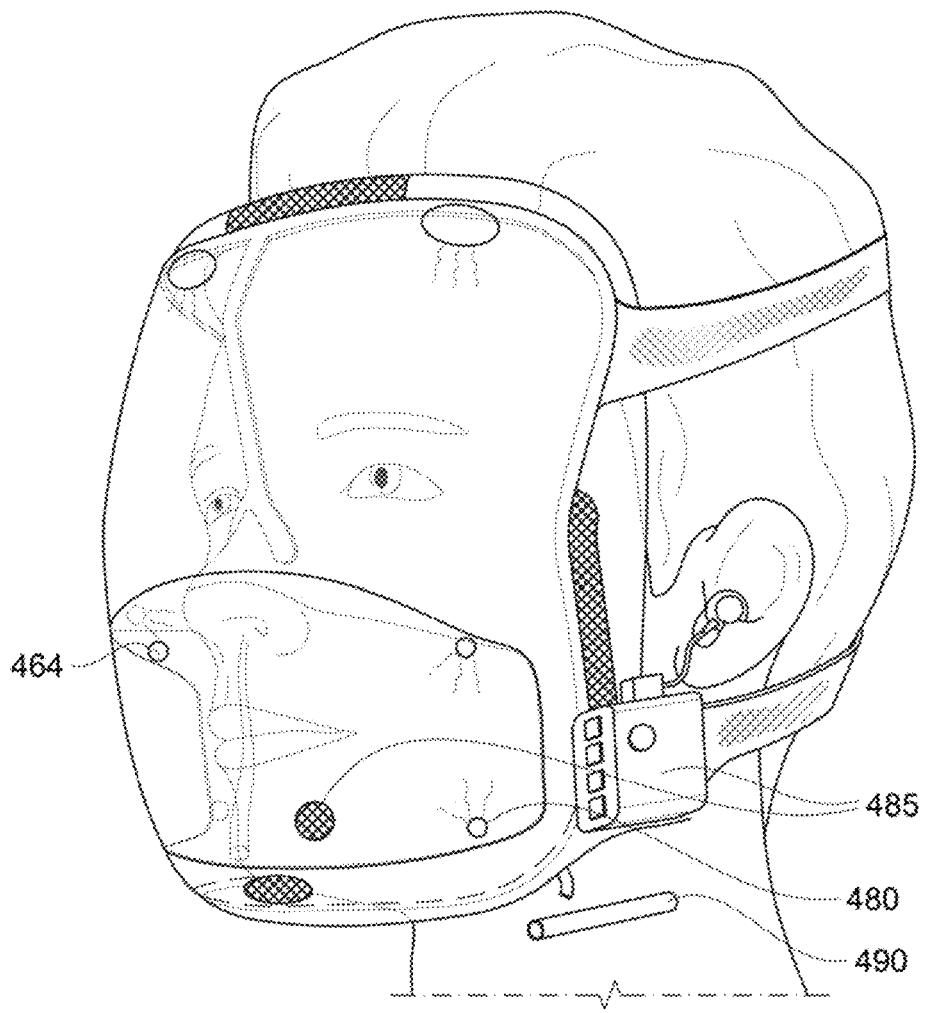

Referring particularly to FIGS. 6-8 in certain preferred embodiments, the face shield is enclosed and includes a detachable and removable/exchangeable section 440 which optionally may contain various accessories such as a manipulatable sneeze/cough guard, or rhinorrhea absorbent tissue role. Referring in particular to FIGS. 7 and 8, the removable/changeable section 440 may contain a one-way valve or other type of air tight drinking port 442 allowing insertion of a straw or other apparatus for liquid consumption, or insertion of a feeding tube for liquid nutrition while maintaining the safety of the respiratory chamber, and without need to remove the remaining personal protective elements. Removable section 440 may be mechanically attachable/detachable using, for example, fittings 450, or in a preferred embodiment, may be magnetically attachable to the face shield preferably using rare earth magnets 460 (see FIG. 9) and/or snap on type clips. Employing magnets has an advantage in that the magnetic field also may attract certain viruses which are polar. Also, radiant far UV-C light beams 462 may be aimed along the attachment seam and/or towards the nasal and/or oropharyngeal areas of the wearer. Additionally, a resiliently deformable self sealing port 464 may be provided to permit flow of pressurized air or oxygen into the face shield to enhance inspired oxygen content for the wearer if this is deemed necessary. Furthermore, optional slightly pressurized air in the respiratory chamber can provide a barrier to air entry when opening an aperture for food or medication.

Further, an array of light sources 480 manufactured or attenuated to emit far UV-C light may be located around the removable lower section for activation when the lower section is removed and exposure to external unfiltered air occurs. Again, slightly pressurized air during removal or exchange can limit the entry of unfiltered air.

Also, if desired, a microphone/amplification/cell phone communication module 485 may be provided, along with auditory and amplification devices for close or distant communication, or to permit the wearer to listen to music, etc.

The face shield may include a removable stylus 490 which emits far UV-C light which may be attachable to the exterior of the shield using magnetic or clip attachments.

The face shield may also contain a mechanical attachment such as a bayonet fixture that can be used with other commercially available respirator filters.

The invention has been described herein using specific embodiments for the purposes of illustration only, and various changes may be made without departure from the spirit and scope of the invention. For example, the device may include LED lenses to focus light beams from the far UV-C light sources onto the nasal and/or oropharyngeal areas of the wearer. Also, a far UV-C LED light source may be attached to a stylus and configured to be aimed at specific therapeutic or potentially contaminated targets of the wearer. Or the far UV-C light source may have an optional multi spectral sensor to identify skin pigment variation and atmospheric attenuation to automatically modulate appropriate dosing adjustments between 0.1-3.0 mJ/cm$^2$ or higher or lower depending on target pathogens and atmospheric conditions. Also, the face shield may include a removeable/exchangeable nose and mouth section to extend from the nasal area to below the mouth of the wearer, preferably removable using magnetic attachments (such as rare earth magnets) to accommodate optional accessories for variable functionality or environmental or therapeutic requirements. The mask or face shield also may include peripheral air fenestrations covered by HEPA or similar or other anti-microbial or decontaminant air filters to provide a two factor method of respiratory protection, especially when used in an enclosed face shield engineered with various features to offer the advantages of a clear visage of the wearer, improved communication, liquid or food consumption while improving respiratory protection of healthcare workers or various groups of the public such as teachers, or the general public during pandemic or other times. The mask or face shield also may include an airtight opening or aperture to allow passage of an endotracheal tube or other suctioning equipment. And, the face shield removeable section may include a mechanism for a cough/sneeze guard having, for example, an absorbable paddle, using a rocking mechanism which may be electrical or manual to move forward and backward. Or the removable section may contain a mechanism for rhinorrhea/nasal secretions absorption, for example, using a double roller for change of absorbable anti microbial material (cloth or paper), which mechanism can be externally controlled as needed. Or the face shield removable section may contain a one way valve or air tight drinking port to admit a straw, feeding tube or other similar apparatus. Or the removable section may contain an aperture for food or medication consumption. Or the removable section may contain a microphone, amplifier or other communication apparatus. The face shield removable section also may contain one or more bayonet style connectors for attachment of a variety of commercially available external devices such as long-lasting filtration devices. Also, if desired, the face shield may include ventilation ports along the top and sides of the face shield, which ventilator ports may include various types of anti-microbial air filters (e.g., HEPA, activated charcoal), and/or a one way expiratory exhaust valve. And, the face shield may include a detachable section in the region of the nose and mouth exchangeable for various accessories, such attachment may be mechanically attached using water tight rubberized or plastic or other material to create occlusive connections and clips, or via magnetic attachments that may double as a viral attractant; such an attractant can be treated with anti-viral nanoparticles to de-activate any virus or sensitive pathogen or provide a target for far UV-C emitted light deactivation. Therefore, the invention should not be regarded as being limited in scope to the specific embodiments disclosed herein, but also to include the scope of the following claims and commensurate with these or similar types of accessories or attachments or embodiments:

We claim:

1. A face mask, respirator, or face shield device providing a respiratory chamber having an interior surface and an exterior surface; and
   one or more or an array of built in or attachable or detachable light sources manufactured or attenuated to emit only germicidal far UV-C wavelengths of between 207-222 nm, configured to direct safe, topical application of far UV-C light of wavelength of between 207-222 nm and, directly into the interior of the face mask, respirator, or face shield device to illuminate the interior of the face mask, respirator, or face shield and to directly illuminate skin of a wearer of the face mask, respirator, or face shield and optionally an exterior surface of said face mask, respirator, or face shield devices for air and surface sterilization of respiratory pathogens.

2. The face mask, respirator, or face shield device of claim 1, wherein the one or more light sources, are attachable/detachable to the face mask, respirator, or face shield device, and/or comprise a u-shaped or other shaped or malleable ring with far UV-C lighted wands or a stylus configured to direct far UV-C light of wavelength of between 207-222 nm to within the interior of the face mask, respirator, or face shield device, or are attachable to at least one nare of the wearer to provide anti-microbial and germicidal sterilization of the respiratory chamber or inhaled/exhaled air or for direct irradiation of nasal or oropharyngeal pathogen reservoirs of the wearer to reduce viral or other pathogen burden combating acquisition or transmission of respiratory pathogens or to treat infection of the wearer by viruses or pathogens.

3. The face mask, respirator, or face shield device of claim 1, wherein the face mask, respirator, or face shield device is re-useable device.

4. The face mask, respirator, or face shield device of claim 1, further comprises an attachable face air filtration barrier, cloth or paper, or is an N95 or higher respirator or surgical mask.

5. The face mask, respirator, or face shield device of claim 1, wherein the face mask, respirator, or face shield device is a face shield or respirator having padding or a skirt formed of malleable material disposed around an internal periphery of the face shield or respirator, to create an enclosed respiratory chamber occlusive to the wearer's skin.

6. The face mask, respirator, or face shield device of claim 1, wherein the face mask, respirator, or face shield device is a respirator which includes a check valve.

* * * * *